(12) United States Patent
Deshpande et al.

(10) Patent No.: US 9,968,565 B2
(45) Date of Patent: May 15, 2018

(54) METHOD FOR PROTECTION AND IMPROVEMENT OF LIVER HEALTH WITH MESO-ZEAXANTHIN COMPOSITIONS

(71) Applicant: OMNIACTIVE HEALTH TECHNOLOGIES LIMITED, Lower Parel, Mumbai (IN)

(72) Inventors: Jayant Deshpande, Charlottetown (CA); Vijaya Juturu, Morristown, NJ (US); Abhijit Bhattacharya, Morristown, NJ (US)

(73) Assignee: OmniActive Health Technologies Limited, Mumbai (IN)

( * ) Notice: Subject to any disclaimer, the term of this patent is extended or adjusted under 35 U.S.C. 154(b) by 0 days. days.

(21) Appl. No.: 15/058,823

(22) Filed: Mar. 2, 2016

(65) Prior Publication Data

US 2016/0256409 A1 Sep. 8, 2016

Related U.S. Application Data

(60) Provisional application No. 62/126,992, filed on Mar. 2, 2015.

(51) Int. Cl.
*A61K 31/047* (2006.01)

(52) U.S. Cl.
CPC .................................. *A61K 31/047* (2013.01)

(58) Field of Classification Search
CPC ..................................................... A61K 31/047
USPC ........................................................ 514/729
See application file for complete search history.

(56) References Cited

U.S. PATENT DOCUMENTS

| 6,218,436 B1 | 4/2001 | Howard et al. |
| 6,329,432 B2 | 12/2001 | Howard et al. |
| 7,435,846 B2 | 10/2008 | Olvera et al. |
| 2004/0022881 A1 | 2/2004 | Hauptmann et al. |
| 2005/0032914 A1 | 2/2005 | Barker et al. |
| 2009/0069417 A1 | 3/2009 | Sharoni et al. |
| 2013/0195985 A1 | 8/2013 | Lepelletier et al. |
| 2014/0187648 A1 | 7/2014 | Howard et al. |

FOREIGN PATENT DOCUMENTS

| CA | 2806009 | 2/2012 |
| CN | 102961394 | 3/2013 |
| GB | 2492881 | 1/2013 |
| KR | 1020040078543 | 4/2006 |
| WO | 2007043046 | 4/2007 |
| WO | 2014155189 | 10/2014 |

OTHER PUBLICATIONS

Xiao et al., PLOS ONE Apr. 2014, vol. 9, Issue 4, e95214, pp. 1-12.*
Wang, Am. J. Pathol. Aug. 2010; 177(2): 713-723.*
International Search Report and Written Opinion for PCT/IB2016/051188, dated Jul. 26, 2016, 6 pages.
Fridous et al., "Hepato-protective potential of carotenoid mezo-zeaxanthin against paracetamol CC1 and ethanol induced toxicity", Indian Journal of Experimental Biology, vol. 49, Jan. 2011, pp. 44-49.
Chamberlain et al., "Protective Effects of the Carotenoid Zeaxanthin in Experimental Nonalcoholic Steatohepatitis", J Dig Dis Sci., vol. 54, May 8, 2009, pp. 1460-1464.

* cited by examiner

*Primary Examiner* — James D. Anderson
(74) *Attorney, Agent, or Firm* — Hamre, Schumann, Mueller & Larson, P.C.

(57) ABSTRACT

A method for protection, treatment and improvement of liver health includes administering a meso-zeaxanthin composition in an effective amount to a subject in need thereof. In particular, methods are described of administering a meso-zexanthin composition to a subject fed with high fat diet (HFD), and studying the effect of meso-zeaxanthin for treatment of fatty liver condition, through evaluation of various parameters such as biochemical indicators, anti-inflammatory markers, and nutritional markers.

3 Claims, 3 Drawing Sheets

METHOD FOR PROTECTION AND IMPROVEMENT OF LIVER HEALTH WITH MESO-ZEAXANTHIN COMPOSITIONS

FIELD

Methods are described that are related to the protection, treatment and improvement of liver health by administering a meso-zeaxanthin composition to a subject in need thereof. More particularly, the methods described herein are related to protection from liver disease as well as improvement of liver health by administering to a subject fed with high fat diet, an effective amount of a meso-zeaxanthin composition comprising meso-zeaxanthin as the active nutrient alone or in combination with other active nutrient(s). Specifically, administering the meso-zeaxanthin composition protects liver from the risk factors associated with cardiometabolic syndrome, such as hyperglycemia and hyperlipidemia, by regulating biochemical parameters of lipid metabolism and lipid content of the liver. The meso-zeaxanthin composition enhances lipid accumulation in adipocytes when administered to a subject in need thereof. Administering the meso-zeaxanthin composition also protects liver by reducing oxidative stress and elevates antioxidant liver enzymes. Administering the meso-zeaxanthin composition protects liver health by reducing cardiometabolic stress in the form of free fatty acids and regulates lipid profile, thus avoiding conditions of fatty liver disease. The method as described herein is comprised of administering meso-zeaxanthin composition in an effective amount to a subject fed with high fat diet. Methods described herein are directed to administering a meso-zeaxanthin composition which is safe for human consumption and can be employed for treatment of non-alcoholic fatty liver disease, arising due to conditions such as cardiometabolic syndrome to improve liver function.

BACKGROUND

Sedentary lifestyle and drastic changes in eating habits are introducing potential health hazards in the modern World. Many of these diseases are chronic and life threatening and put burden on overall health system. Lifestyle diseases such as hypertension and diabetes are prevailing along with obesity and dyslipidemia. There are many concurrent effects of obesity on overall health and fatty liver disease is one of the most critical diseases which are affecting majority of the population. Existence of some fat in liver is normal; but fatty liver disease is a condition where fat makes up more than 5%-10% of the weight of an individual's liver. This may be alcoholic or non-alcoholic liver disease and can lead to serious complications related to lipid imbalance and increased free fatty acids, thus imposing risk of cardiometabolic syndrome.

Fat from a person's diet is usually metabolized by the liver and other tissues. A fatty liver is the result of the excess fat in liver cells. Fatty tissue slowly builds up in the liver when a person's diet exceeds the amount of fat his or her body can handle. Other reasons for accumulation of fat in the liver could be the transfer of fat from other parts of the body or the inability of the liver to change it into a form that can be eliminated. Once there is build-up of excess fat, the liver becomes vulnerable to further injury, which may result in inflammation and scarring of the liver. For example, alcoholic liver disease is observed in 90 to 100% of the U.S. population who abuse or overuse alcohol. Fatty liver can occur after drinking moderate or large amounts of alcohol. It can even occur after a short period of heavy drinking (acute alcoholic liver disease). Non-alcoholic fatty liver disease is a condition which starts with fat accumulation in the liver without excessive alcohol consumption. It is strongly associated with metabolic syndrome in the form of obesity, and insulin resistance combined with dyslipidemia. Non-alcoholic fatty liver disease is now the most common cause of chronic liver disease for example in the U.S. which can lead to permanent liver damage. The liver may enlarge and, over time, liver cells may be replaced by scar tissue, leading to cirrhosis, liver failure, liver cancer, and liver-related death. Non-alcoholic fatty liver disease also increases the risk of heart disease in children who are overweight or obese, thus affecting overall population.

Although some of the potential causes of fatty liver disease include long term medications, viral hepatitis, and malnutrition, the risk of developing fatty liver disease is occurring more in patients with high cholesterol, triglycerides, diabetes, in overweight or obese people. Diagnosis of fatty liver disease can be done through blood tests for liver enzymes, imaging studies and liver biopsy. But there is no specific treatment at this time for this disease. Although the trials are ongoing for evaluating effectiveness of certain antioxidants and newer diabetes medications in treating fatty liver disease, current treatment options are based on lifestyle modification, weight loss and physical activity in order to reduce the amount of fat in the liver. Thus there is a need for exploring alternative treatment options which would be safe, natural and induce favorable body conditions to combat such a chronic disease.

Earlier references reveal use of meso-zexanthin as dietary supplement for different health benefits.

Patent application GB2492881 relates to a composition comprising xanthophyll carotenoid meso-zeaxanthin (MZ) for use as a dietary supplement or food additive for oral consumption for improving the visual performance of a human subject, in particular, a human subject not experiencing age-related macular degeneration (AMD).

U.S. patent application US20140187648 provides a method of improving the visual performance of a human subject, the method comprising the steps of: identifying a subject likely to have one or more of (i) low macular pigment concentration; (ii) low visual performance or (iii) an atypical 'central dip' macular pigment distribution; and administering an amount of a macular pigment-containing composition sufficient to improve the visual performance of the subject, wherein the macular pigment-containing composition comprises meso-zeaxanthin, lutein and/or zeaxanthin.

Patent application US20130195985 relates to a composition comprising an enzyme selected from the group comprising superoxide dismutase (SOD) and SOD mimics and the like, in association with lutein and at least one stereoisomer of zeaxanthin (i.e. meso-zeaxanthin); further the composition may be included in a functional food or dietary supplement, for use in treating, preventing or stabilizing a disease, condition or disorder of the eye associated to oxidative stress, comprising administering to a subject in need thereof a medicament or a pharmaceutical composition according to the invention.

Canadian patent application CA2806009 relates to a composition comprising a natural extract containing anthocyanins, an agent for enhancing vigilance, and optionally at least one of lutein, zeaxanthin, meso-zeaxanthin and astaxanthin; the composition being in an unitary dosage form adapted to transmucosal administration, the unitary dosage form preferably being a chewing gum, an orodispersible/orodisintegrating tablet or film or a buccal spray.

U.S. Pat. No. 7,435,846 relates to a process for obtaining stable microemulsions that are composed of a solubilizate of derivatives of oxycarotenoids of short chain organic acids, selected from the group consisting of diacetates and dipropionates of lutein, 3'epilutein, zeaxanthin, iso-zeaxanthin, meso-zeaxanthin, capsanthin, capsorubin, astaxanthin, and cryptoxanthin monoacetate and monopropionate, wherein the microemulsions can be administered to humans as a supplement to prevent and protect cells and tissues from the damaging effect of free radicals and singlet oxygen, as well as to prevent the risk of cancers and stroke.

U.S. patent application US20050032914 describes a method of making a composition for the improvement of visual performance in the darkness comprising incorporating a carotenoid into a medicament, a food, or a beverage, wherein the carotenoid is selected from lutein, zeaxanthin, meso-zeaxanthin, astaxanthin, or esters thereof, or canthaxanthin, or from compounds having vitamin A activity or precursors thereof, or mixtures of the foregoing.

U.S. Pat. No. 6,329,432 provides meso-zeaxanthin compositions for pharmaceutical use and use of meso-zeaxanthin to increase the deposition of macular pigment in the human eye, and for the therapeutic treatment or prophylaxis of diseases and disorders of the macula, in particular age-related macular degeneration (AMID).

Another U.S. Pat. No. 6,218,436 relates to a method of therapy or prevention of age-related macular degeneration in a human subject by increasing deposition of yellow macular pigment in the macula of an eye of the subject, the method comprising orally administering to the subject a sufficient amount of meso-zeaxanthin to increase the serum concentration of carotenoid(s) in the subject to at least 0.5 µg/ml and maintain the increased serum carotenoid concentration at or above 0.5 µg/ml for at least 14 days, and at least until the macular concentration of carotenoid(s) has achieved equilibrium.

PCT patent application WO2007043046 relates to a method of preventing the onset of cancer in a subject, comprising the step of administering to said subject a pharmaceutical composition comprising a carotenoid oxidation product, in an amount effective to prevent the onset of cancer in said subject; wherein the carotenoid is a tomato carotenoid, preferably the carotenoid is selected from the group consisting of lycopene, $\alpha$- and $\beta$-carotene, phytoene, phytofluene, lutein, zeaxanthin, $\alpha$- and $\beta$-cryptoxanthin, canthaxanthin, astaxanthin, and combinations thereof.

Korean patent application KR1020040078543 relates to compositions containing vitamin E compounds in addition to carotenoid compounds. In case of administering capsules each containing natural lycopene, natural $\beta$-carotene, natural $\alpha$-carotene, and other natural carotenoids and $\alpha$-tocopherol, these compositions are significantly efficacious in preventing liver cancer in humans.

Firdous, Sindhu et al (Indian Journal of Experimental Biology-49, pages 44-49, January 2011) describes the effect of meso-zeaxanthin on liver to treat drug-induced hepatotoxicity and liver injury. It was shown that meso-zeaxanthin pretreatment reduced elevated liver enzymes and thus nullified effect of liver toxicity.

Chamberlain, Hall, Patel et al (J Dig Dis Sci. 54, pages 1460-1464, May 2009) relate to effects of carotenoid zeaxanthin in treatment of liver injury in Mongolian gerbils, fed with a methionine-choline-deficient diet, for creating the condition similar to human non-alcoholic steatohepatitis (NASH). According to this study, zeaxanthin improves histopathological changes and liver injury, caused due to methionine choline-deficient (MCD) diet.

SUMMARY

Even though the prior art describes effects of Meso-zeaxanthin for combating eye disorders, or to prevent drug induced hepatotoxicity or liver injury and histopathological changes in liver tissue due to nutrition deficient diet, there is no teaching on method for using meso-zeaxanthin composition for protective effect on liver from progression of condition such as non-alcoholic fatty liver disease, which occurs due to hyperglycemia or hyperlipidemia. Further no prior art relates to the effect of meso-zeaxanthin on improvement of liver health by reduction of risk factors related to cardiometabolic syndrome, such as glucose levels, lipid profile, body weight, insulin levels or reduction of oxidative stress, for treatment of liver disease.

Carotenoids such as lutein, zeaxanthin and meso-zeaxanthin are powerful antioxidants and protect the eye from aging effect because of this property. Meso-zeaxanthin is the most powerful anti-oxidant of these three carotenoids and also exhibits additional protective effects like anti-mutagenic, singlet oxygen quenching and potential to induce phase II enzymes, chemo protective and anti-carcinogenic effects, because of its inherent effect. Meso-zeaxanthin could scavenge superoxide, hydroxyl, nitric oxide, 2,2-diphenyl-1-picrylhydrazyl (DPPH) and 2,2'-azino-bis(3-ethylbenzothiazoline-6-sulphonic acid) (ABTS) radicals and inhibit tissue lipid peroxidation and prevents cellular damage. Meso-zexanthin increases the levels of antioxidant enzymes like catalase, superoxide dismutase and glutathione peroxidase.

The inventors in this application have carried out rigorous experimentation that show the effect of meso-zeaxanthin in protecting liver by effectively managing multiple risk factors leading to fatty liver disease, which is not reported anywhere in the prior art. Methods herein relate to administering a meso-zeaxanthin composition to a subject in an effective amount, which is beneficial for protection, treatment and improving liver health. When the meso-zeaxanthin composition is administered in an effective amount to a subject fed with high fat diet, it protects liver by reducing oxidative stress and enhances lipid accumulation in adipocytes. The meso-zeaxanthin composition also elevates liver antioxidant enzymes and improves liver health by reducing cardiometabolic stress and/or metabolic syndrome in the form of free fatty acids. Thus the method of administering the meso-zeaxanthin composition protects liver from progression of underlying disease conditions such as hyperglycemia or hyperlipidemia, so as to avoid development of fatty liver conditions, and maintains normal anatomical structure, integrity and function of liver tissues during both healthy and disease condition, when administered in an effective amount. The meso-zeaxanthin composition used in the methods herein is safe and convenient for administration and improves liver health through enhancement of detoxification of these organs.

"High fat diet" (HFD) is a diet which is rich in fat content or calories coming out of fat portion of the diet. In one example, a high fat diet for humans contains about 40-55% calories from fat. In one example, a high fat diet can be about 27% calories coming from carbohydrates, about 58% (or as low as about 40%) calories coming out of fats and about 15% calories coming from protein portion in total % calories in diet. Generally, for animals 40 to 55% of fat calories can be considered HFD. It will be appreciated that this range can vary for example depending upon the animal.

"Risk factors" herein, which are the subject of Applicant's study, are meant to include biological markers such as metabolic health markers, lipid profile, obesity end points, inflammatory cytokines, adiponectin, antioxidant enzymes as well as liver enzymes, which are indicators of cardiometabolic syndrome and are related to specific conditions such as obesity, diabetes and hypertension.

"Risk factors" herein, which are the subject of Applicant's study, are meant to include those related to obesity, hypertension, diabetes, cardiovascular disease, inflammation which may cause non-alcoholic fatty liver (NAFL). Treating and/or prevention of these risk factors are more important to reduce the risk of NAFL and further progression which may lead to liver failure and liver cancer. In Applicant's study, meso-zeaxanthin reduced such risk factors, regulated liver enzyme activity, and reduced the risk of NAFL which is a prevention as well as treatment of liver disease or condition.

Non-alcoholic fatty liver disease (NAFLD) is the buildup of extra fat in liver cells that is not caused by alcohol. It is normal for the liver to contain some fat. However, if more than 5%-10% percent of the liver's weight is fat, then it is called a fatty liver (steatosis). NAFLD tends to develop in people who are overweight or obese or have diabetes, high cholesterol or high triglycerides. Rapid weight loss and poor eating habits also may lead to NAFLD. NAFLD may cause the liver to swell (steatohepatitis). A swollen liver may cause scarring (cirrhosis) over time and may even lead to liver cancer or liver failure. NAFLD often has no symptoms. When symptoms occur, they may include fatigue, weakness, weight loss, loss of appetite, nausea, abdominal pain, spider-like blood vessels, yellowing of the skin and eyes (jaundice), itching, fluid buildup and swelling of the legs (edema) and abdomen (ascites), and mental confusion. NAFLD is initially suspected if blood tests show high levels of liver enzymes.

Pathways of regulation can include glucose metabolism, lipid metabolism, inflammatory pathways, and oxidative stress and antioxidant pathways. The causes for accumulation of fat in liver cells are due to several risk factors, such as described above. For example, abnormal and/or disturbed metabolism and/or impaired pathways may be the subject of regulation, e.g. which may be exhibited in conditions of disturbed/impaired lipid profile and/or hyperlipidemia.

"Liver enzymes" herein are meant to include but are not limited to for example aminotransferases. They include aspartate aminotransferase (AST or SGOT) and alanine aminotransferase (ALT or SGPT). In addition to AST and ALT, other enzymes can include but are not limited to alkaline phosphatase, 5' nucleotidase, and gamma-glutamyl transpeptidase (GGT), which are located in the liver. It will be appreciated that other ways may be used to diagnose the liver disease or condition, such as by ultrasound and diagnosis of liver hypertrophy (increase in liver size) due to fatty liver and ascites.

"Liver enzymes" herein are meant to include those that can reduce cholesterol and free fatty acids, which are a part of Applicant's study.

Regulation of liver tissue gene proteins is meant to include those genes that support mechanisms of action on how meso-zeaxanthin can reduce oxidative genes, and improve antioxidant capacity. Applicant's study includes data on thiobarbituric acid reactive substances (TBARS) and other oxidative stress and antioxidant data in blood.

Applicant's study is also designed to show how fat intake affects liver and other associated conditions such as obesity, diabetes and cardiovascular disease (CVD), which may be caused by disturbance or impairment in carbohydrate and lipid metabolism which can lead to fatty liver.

In an embodiment, a method relates to administering a meso-zeaxanthin composition in an effective amount and is evaluated for its beneficial effect on the liver in a subject.

In an embodiment, the method of administering a meso-zeaxanthin composition in an effective amount to a subject in need thereof, is evaluated for the improvement of liver health.

In an embodiment, the meso-zeaxanthin composition includes meso-zeaxanthin as the active nutrient alone or in combination with one or more other active nutrient(s). In an embodiment, the meso-zeaxanthin is present in the meso-zeaxanthin composition in a higher weight percentage relative to other active nutrient(s) present in the meso-zeaxanthin composition. In an embodiment, the meso-zeaxanthin is present in the meso-zeaxanthin composition at or about 80% by weight relative to the total amount of active nutrient(s). In an embodiment, the meso-zeaxanthin is present in the meso-zeaxanthin composition by at 80% by weight relative to the total amount of active nutrient(s). In an embodiment, the meso-zeaxanthin is present in the meso-zeaxanthin composition at higher than 80% by weight relative to the total amount of active nutrient(s).

In an embodiment, the meso-zeaxanthin is present in the meso-zeaxanthin composition by at least 80% by weight relative to the total amount of active nutrient(s) in the composition.

In an embodiment, the meso-zeaxanthin is present in the meso-zeaxanthin composition up to 90% by weight relative to the total amount of active nutrient(s), or about 90% by weight relative to the total amount of active nutrient(s).

In an embodiment, the meso-zeaxanthin is present in the meso-zeaxanthin composition in the range of at least 80% by weight to at or about 90% by weight relative to the total amount of active nutrient(s) in the composition.

In an embodiment, the meso-zeaxanthin is present in the meso-zeaxanthin composition in the range of at or about 80% by weight to at or about 90% by weight relative to the total amount of active nutrient(s) in the composition.

In an embodiment, the meso-zeaxanthin is present in the meso-zeaxanthin composition in the range of at or about 85% by weight to at or about 90% by weight relative to the total amount of active nutrient(s) in the composition.

In an embodiment, the remaining active nutrients being other carotenoids including trans-lutein and R,R zeaxanthin, and other carotenoids including beta-carotene, lycopene, betacryptoxanthin and astaxanthin, and combinations thereof.

In an embodiment, a method of administering a meso-zeaxanthin composition includes administering in a dose of at or about 0.1 to at or about 200 mg/kg body weight to a subject fed with high fat diet, to protect liver, to improve liver health or treat liver disease such as non-alcoholic fatty liver disease. In an embodiment, a method of administering a meso-zeaxanthin composition includes administering in a dose of at or about 0.1 mg/kg to at or about 100 mg/kg body weight to an individual in need thereof, to protect liver, to improve liver health, and/or treat liver disease, such as for example non-alcoholic fatty liver disease. In an embodiment, the relative amount of meso-zeaxanthin in the meso-zeaxanthin composition is as described above and below herein.

In an embodiment, a method of administering a meso-zeaxanthin composition includes administering in a dose of at or about 10 mg/kg to at or about 150 mg/kg body weight to a subject fed with high fat diet, to protect liver, to improve liver health or treat liver disease such as non-alcoholic fatty liver disease. In an embodiment, the relative amount of meso-zeaxanthin in the meso-zeaxanthin composition is as described above and below herein.

In an embodiment, a method of administering a meso-zeaxanthin composition includes administering in a dose of at or about 50 mg/kg to at or about 100 mg/kg body weight to a subject fed with high fat diet, to protect liver, to improve liver health or treat liver disease such as non-alcoholic fatty liver disease. In an embodiment, the relative amount of meso-zeaxanthin in the meso-zeaxanthin composition is as described above and below herein.

In an embodiment, a method of administering a meso-zeaxanthin composition in an effective amount to a subject fed with high fat diet enhances fat accumulation in adipocytes and helps in treatment of fatty liver disease.

In an embodiment, a method of administering a meso-zeaxanthin composition in an effective amount to a subject in need thereof maintains normal anatomical structure, integrity and function of liver tissues during both healthy and disease condition.

In an embodiment, a method for protection, improvement and treatment of liver health, comprising administering a meso-zeaxanthin composition in an effective amount to a subject fed with high fat diet; wherein the meso-zeaxanthin composition regulates lipid content, biochemical indicators of lipid metabolism, and/or general nutrition parameters, and/or reduces oxidative stress, and is thus useful for treatment of fatty liver disease.

In an embodiment, a method, wherein the step of administering a meso-zeaxanthin composition includes regulating blood glucose as one of the biochemical indicators of lipid metabolism, when administered to a subject fed with high fat diet.

In an embodiment, a method, wherein the step of administering a meso-zeaxanthin composition includes regulating insulin as one of the biochemical indicators of lipid metabolism, when administered to a subject fed with high fat diet.

In an embodiment, a method, wherein the step of administering a meso-zeaxanthin composition to a subject fed with high fat diet, includes regulating free fatty acids, as one of the biochemical indicators of lipid metabolism.

In an embodiment, a method, wherein the step of administering a meso-zeaxanthin composition to the subject fed with high fat diet includes regulating adiponectin to increased levels and regulating general nutrition parameters such as body weight, liver weight, useful for treatment of liver disease.

In an embodiment, administering a meso-zeaxanthin composition in an effective amount to a subject fed with a high fat diet protects liver and reduces progression of fatty liver disease conditions, by minimizing the effects of risk factors associated with cardiometabolic syndrome.

In an embodiment, a method, wherein the step of administering a meso-zeaxanthin composition in an effective amount to a subject fed with a high fat diet includes regulating lipid content in liver, blood lipid profile, liver antioxidant enzymes and also reducing oxidative stress on liver.

Thus the methods herein of administering a meso-zeaxanthin composition in an effective amount to a subject in need thereof are useful for protection, treatment and improvement of liver function.

Meso-zeaxanthin compositions herein can be useful for liver protection, and which can reduce free fatty acids and reduce certain risk factors associated with cardiometabolic and/or metabolic syndrome, such as for example diabetes, hypertension, hyperlipidemia, and the like.

Meso-zeaxanthin compositions herein can improve liver health by inhibiting liver enzymes, and by enhancement of a detoxification process.

Meso-zeaxanthin compositions herein can help maintain normal anatomical structure, integrity, and function of liver tissues during both healthy conditions and in diseased conditions, when administered in effective amounts.

Meso-zeaxanthin compositions herein can protect liver and reduce progression of fatty liver disease conditions, by minimizing the effects of risk factors associated with cardiometabolic syndrome, in an individual in need thereof.

DETAILED DESCRIPTION

Figure 1A:
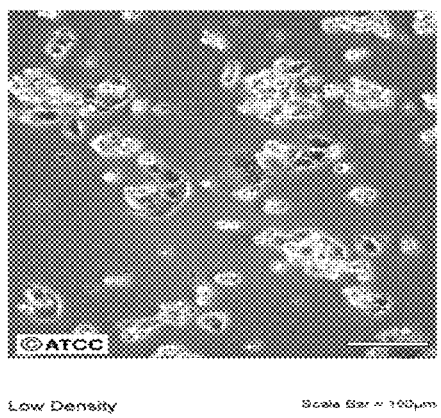
FIG. 1A shows a low density micrograph of fatty liver cells exhibiting fatty condition.
Figure 1B:
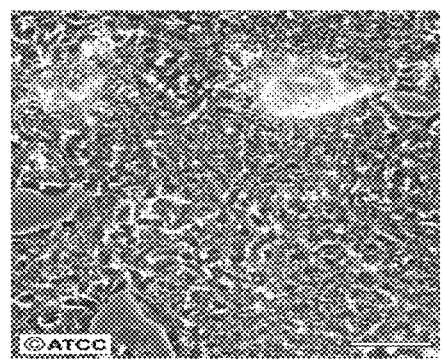
FIG. 1B shows a high density micrograph of fatty liver cells exhibiting fatty condition.

A method of protection, improvement and treatment of liver health includes administering a meso-zeaxanthin composition in an effective amount to a subject in need thereof. The method helps to maintain normal anatomical structure, integrity and physiological function of liver tissues during both healthy and disease condition, by administering a meso-zeaxanthin composition in an effective amount to a subject in need thereof. The method helps in treating the risk factors associated with cardiometabolic syndrome, thus protecting liver from progressing to a disease condition such as fatty liver disease.

Overnutrition/obesity is the major cause of non-alcoholic fatty liver disease (NAFLD) and its advanced form non-alcoholic steatohepatitis (NASH). Steatosis is the process by which abnormal retention of lipids occurs within a cell and fatty liver disease (FLD), is a reversible condition wherein large vacuoles of triglyceride fat accumulate in liver cells via steatosis. The condition is also associated with other diseases that influence fat metabolism. When this process of fat metabolism is disrupted, the fat can accumulate in the liver in excessive amounts, thus resulting in a fatty liver. Accumulation of fat may also be accompanied by a progressive inflammation of the liver (hepatitis), called steatohepatitis. By considering the contribution by alcohol, fatty liver may be termed alcoholic steatosis or non-alcoholic fatty liver disease (NAFLD), and the more severe forms as alcoholic steatohepatitis (part of alcoholic liver disease) and non-alcoholic steatohepatitis (NASH). There is need of treating this liver disease, in a subject in need thereof and also taking care to avoid the disease by identifying the symptoms and cardiometabolic risk factors earlier through routine examination for protection and improvement of liver health. Therefore the methods and the compositions herein help take care of liver health.

The method as described herein is comprised of administering a meso-zeaxanthin composition in an effective amount to a subject in need thereof for protection, treatment and improvement of liver health and any liver disease, such as fatty liver disease. In an embodiment, the method can include the step of monitoring biochemical indicators of lipid metabolism, liver lipid contents, general nutrition parameters, levels of antioxidant liver enzymes and the like.

In an embodiment, the effect of administering a meso-zeaxanthin composition to a subject in an effective amount is evaluated for protection, treatment and improvement of liver function, in normal, healthy as well as a disease condition.

The terminology 'subject' is commonly used in the specification to refer to a human being, animal, or mammal under test, being treated with the meso-zeaxanthin composition. The subject in need thereof may be healthy or showing some symptoms of liver disease or compromised liver function. As per the method of evaluation, the subject is fed with a high fat diet and the parameters such as biochemical indicators (glucose, insulin, free fatty acids), lipid profile, general nutrition parameters (body weight, liver weight, fat index, liver weight:body weight) are checked before and after administration of meso-zeaxanthin composition in an effective amount.

In an embodiment, a method includes regulating one or more parameters related to liver health after administration of meso-zeaxanthin to a subject fed with high fat diet.

Regulation of parameters in terms of increased and/or decreased levels indicate use of meso-zeaxanthin for treatment of liver disease as well as improvement of liver health due to certain cardiometabolic health risk (CHR) factors such as hypertension, obesity, diabetes, hyperlipidemia in a subject.

In an embodiment, a meso-zeaxanthin composition used as per the methods herein is obtained by natural resources and is safe for administration and thus useful for nutraceutical/food and/or therapeutic purposes.

In an embodiment, the meso-zeaxanthin composition herein is obtained by thermo-chemical isomerization from lutein and lutein esters or extracts having lutein and lutein esters. Particularly the composition is enriched with meso-zeaxanthin, containing at least 80% by weight of (trans, 3R,3'S,meso)-zeaxanthin based on a total xanthophyll content and the remaining being (trans, R,R)-lutein, (trans, R,R)-zeaxanthin and other carotenoids.

In another embodiment, the thermo-chemical isomerization process for preparation of meso-zeaxanthin composition enriched with (trans,3R,3'S,meso)-zeaxanthin comprising steps of (i) mixing lutein or an extract containing lutein ester with GRAS solvent and alkali; (ii) heating the resulting mixture under stirring at a temperature in the range of 80-200 degree C.; maintaining the mixture at this temperature for a period in the range of 3 to 36 hrs; (iii) washing the resultant product with aqueous alcohol and filtering to recover the crude xanthophylls composition containing (trans,3R,3'S,meso)-zeaxanthin, (trans, R,R)-lutein and (trans, R,R)-zeaxanthin and trace amounts of other carotenoids; and (iv) purifying the resulting product with polar and non polar solvents.

The reaction of lutein ester saponification and of lutein isomerisation gives the meso-zeaxanthin, which is further subjected to two stage purification steps. In an embodiment, (trans,3R,3'S,meso)-zeaxanthin in an amount of >90% based on the total xanthophylls content can be obtained.

According to the process the GRAS solvent used in step (i) is selected from aromatic primary alcohols, being phenyl carbinol and p-isobenzyl alcohol, wherein the alkali used is selected from sodium hydroxide or potassium hydroxide. Further the ratio of the lutein material, solvent and the alkali used in step (i) is in the range of 1 to 0.5:0.5 to 1.0:1.0. The lutein material is derived from plant source, preferably from marigold flowers.

In an embodiment, the meso-zeaxanthin composition used in the method herein may be used in the form selected from the group of beadlets, micro-encapsulated powders, oil suspensions, liquid dispersions, capsules, pellets, ointments, soft gel capsules, tablets, chewable tablets or lotions/liquid preparations. The meso-zeaxanthin composition may be provided with a coating which helps preserve the original quality characteristics.

In some embodiments, compositions of meso-zeaxanthin can be found in Applicant's U.S. Pat. No. 8,212,063, which is incorporated herewith by reference. In an embodiment, the amount of meso-zeaxanthin in the meso-zeaxanthin composition is measured by high performance liquid chromatography (HPLC) and/or by chiral analysis.

In an embodiment, a method is provided for protection, treatment and improvement of liver health by administering a meso-zeaxanthin composition in an effective amount to a subject in need thereof.

Liver enzymes play an important role in metabolism activities and it is an important site of fat metabolism. When this function is impaired due to variety of reasons, fat accumulation occurs in the liver, thus resulting into cirrhosis and increased risk of other cardiometabolic syndrome and or metabolic syndrome such as diabetes, hypertension, lipid profile, and one or more risk factors associated with these syndromes or in combination with other associated conditions.

Adipose tissue in the body are meant to store excess fat and utilize it for protection of body organs by cushioning effect and providing body energy and heat in situations of scarcity.

In one embodiment, a method as described herein provides for the administration of a meso-zeaxanthin composition in an effective amount to a subject in need thereof, enhances accumulation of fat in adipocytes, thus reducing fatty load on liver.

In one embodiment, a method also provides for the administration of a meso-zeaxanthin composition which improves liver function by reducing oxidative stress and elevating liver antioxidant enzymes.

In one important embodiment, a method provides for the administration of a meso-zeaxanthin composition in an effective amount to a subject in need thereof helps to treat fatty liver disease. The fatty liver disease may be non-alcoholic or alcoholic, more specifically the meso-zeaxanthin composition is used to treat non-alcoholic fatty acid disease, which progresses as a result of conditions such as hyperglycemia or hyperlipidemia, as associated risk factors due to cardiometabolic stress.

In one embodiment, the meso-zeaxanthin composition is evaluated in vitro and/or in vivo to check its effect on regulating parameters such as effect on lipid content of hepatic cell model, effect in rat model to check parameters such as biochemical indicators of lipid metabolism, lipid profile, general nutrition parameters such as body weight, liver weight and oxidative stress. These evaluations are measured in the form of regulations (increased or decreased level) of said parameters to decide effect of meso-zeaxanthin composition in subjects having fatty liver disease induced through administration of high fat diet. Parameters are checked before and after administration of meso-zeaxanthin composition in rat models which are fed with high fat diet.

In one embodiment, a meso-zeaxanthin composition is evaluated for its effect for protection, treatment and improvement of liver health in a subject having healthy or disease condition.

In one embodiment, the effect of meso-zeaxanthin on fatty liver and cardiometabolic health risk (CHR) in insulin resistance is evaluated in Sprague Dawley rats by administering high fat diet. The expression of proteins associated with oxidative stress as well as inflammatory response is measured in the liver. CHR (glucose and lipid profile) and the body weight of animals are also measured.

The Examples given below are provided to illustrate method for protection and improvement of liver health by administering meso-zeaxanthin composition. While the compositions and methods have been described in terms of illustrative embodiments, certain modifications and equivalents will be apparent to those skilled in the art and are intended to be included within the scope of the compositions and methods herein. The details and advantages of which are explained hereunder in greater detail in relation to non-limiting exemplary illustrations.

EXAMPLES

Example 1: In Vitro Study Using Fatty Liver Model Using HepG2 (ATCC HB-8065)

HepG2 cells were seeded at a density of $5 \times 10^4$ cells/mL in 24 well plates and cultured to 100% confluency. Once 100% confluent, HepG2 Growth Media (ATCC-formulated Eagle's Minimum Essential Media (EMEM) 500 mL+10% FBS-50 mL+1% pen/strep antibiotic-5 mL) was supplemented with fetal bovine serum (FBS) Free Growth Media (1 mL per well) for 24 hours. Following 24 hour FBS-free conditions, cells were treated with differing concentrations of Oleic Acid (0.5, 1.0, 1.5, 2.0 mM; Sigma O3008) to induce fatty liver conditions.

From preliminary Adipored Staining data, 1.5 mM Oleic Acid (OA) was deemed the most appropriate concentration of OA to induce maximum steatosis (accumulation of large vacuoles of triglyceride fat in liver cells—thus it is abnormal retention of lipids within a cell) while remaining non-cytotoxic.

HepG2 cells were treated with the following concentrations of the desired extract or positive controls in combination with 1.5 mM Oleic Acid and the effect on lipid content was noted in Table 1.

Test Substances:
Meso-zeaxanthin composition (MZ)
1.5 mM Oleic Acid+50 ug/mL MZ
1.5 mM Oleic Acid+100 ug/mL MZ
Positive Controls:
1.5 mM Oleic Acid+100 uM Rutin
1.5 mM Oleic Acid+10 uM Statin

TABLE 1

Effect of MZ on lipid content in hepatocytes

| Groups | Lipid Content | % Decrease in Lipid Content |
|---|---|---|
| control | 15617 | |
| 1.5 mM Oleic acid OA | 29511.33 | |
| 1.5 mM OA + 50 ug/mL meso | 25746.33 | 13% |
| 1.5 mM OA + 100 ug/mL meso | 22266.75 | 25% |
| 1.5 mM OA + 10 uM Statin | 22226 | 25% |
| 1.5 mM OA + 100 uM Rutin | 23088.67 | 22% |

It was observed that meso-zeaxanthin supplementation at concentration of 100 ug/mL causes decrease in lipid content in hepatocytes, which is equivalent to effect of decrease in lipid content by equivalent amount of positive control statin.

Example 2: Effect of Meso-Zeaxanthin Composition (MZ) on Fatty Liver in Rat Models The research is modeled to give a high fat diet (HFD) to animals to induce insulin resistance. Once they insulin resistance is developed, changes can be seen in certain liver parameters. These changes are reduced by administration of MZ, thus showing use of MZ for liver protection or treatment.

Animals and Diets:
Eight weeks old male Sprague-Dawley rats, weighing 180±20 g, were used throughout the study. The animals were reared at 22±2° C., 55±5% humidity and a 12/12 h light/dark cycle and provided rat chow and water ad libitum. All experiments were conducted under the National Institutes of Health's Guidelines for the Care and Use of Laboratory Animals, and approved by the Ethics Committee of the Veterinary Control Institute. The control (12% calories from fat) and high-fat (42% calories from fat) diet, as per the AIN-93 recommendations, composed of casein (20%), soybean oil (7%), wheat starch (53.2%), sucrose (10%), potato starch (5%), L-cysteine (0.3%), and a vitamin (1%) and mineral (3.5%) mix. The high-fat diet (HFD) was obtained from the basal AIN-93 diet, by replacing wheat starch with fat (15% beef tallow, wt/wt, and 10%, wt/wt, soybean oil. For induction of obesity (insulin resistance), rats were fed with HFD for 12 weeks.

Experimental Protocol:
After acclimatization for 2 weeks, twenty eight rats were randomly divided into the following four groups: (1) Rats fed with control standard chow (C), (2) Rats fed the high fat diet (40% of calories as fat, HFD), (3) C+MZ (100 mg/kg body weight) and (4) HFD+MZ (100 mg/kg body weight). The animals were supplemented with MZ daily for 12 weeks. Meso-zeaxanthin composition (MZ) dose (5% suspension) was prepared by dissolving MZ in sunflower oil. At the end of the experiment, the blood was collected after an overnight fast. All rats were sacrificed by cervical dislocation and their retinas were removed and processed for biochemical and Western blot analyses.

The MZ composition in the experiment can be defined as an oil suspension, which contains at or about 80% by weight of meso-zeaxanthin relative to the other active ingredients, in this case carotenoids, including trans-lutein, R,R zeaxanthin. The 5% suspension means that per 100 ml of oil, in this example sunflower oil, there is at or about 5 gm of the MZ composition in the oil suspension. It will be appreciated that similar results may be obtained with the relative amount of meso-zeaxanthin in the overall MZ composition being as high as at or about 85% by weight to at or about 90% by weight.

Serum Biochemical Estimations:
Serum was prepared by centrifuging the blood at 3,000×g for 10 min and used for the analyses of glucose, insulin and malondialdehyde (MDA). Serum glucose concentration was measured using an automatic analyzer (Samsung LABGEO PT10, Samsung Electronics Co, Suwon, Korea). Repeatability and device/method precision of LABGEO PT10 was established according to the IVR-PT06 guideline. Serum insulin levels were measured with the Rat Insulin Kit (Linco Research Inc, St. Charles, Mo., USA) by enzyme-linked immunosorbent assay (ELISA) (Elx-800, Bio-Tek Instruments Inc, Vermont, USA).

Lipid peroxidation was measured in terms of malondialdehdye (MDA), a major product of membrane lipid peroxidation, according to the method described by Karatepe (Karatepe, 2004). MDA in retinal was measured by high performance liquid chromatography (HPLC, Shimadzu, Tokyo, Japan) using a Shimadzu UV-vis SPD-10 AVP detector and a CTO-10 AS VP column and a mobile phase consisting of 30 mM $KH_2PO_4$ and methanol (82.5:17.5, v/v, pH 3.6) at a flow rate of 1.2 ml/min. Column effluents were monitored at 250 nm. The volume of the sample injected into high performance liquid chromatography (HPLC) was 20 µl. Retina homogenate (10%, w/v) was prepared in 10 mM phosphate buffer (pH 7.4), centrifuged at 13,000×g for 10 min at 4° C. The resulting supernatant was collected and stored at −80° C. for the estimation of MDA.

Superoxide dismutase (SOD), catalase (CAT) and glutathione peroxidase (GPx) in the homogenized tissue were measured using a commercial kit (Cayman Chemical, Ann Arbor, Mich., USA) according to the manufacturer's instructions.

Western Blot Analyses:

For Western blot, protein extraction was performed by homogenizing the retina in 1 ml ice-cold hypotonic buffer-A, containing 10 mM HEPES (2-[4-(2-hydroxyethyl)-1-piperazinyl]ethanesulfonic acid), pH 7.8, 10 mM KCl, 2 mM $MgCl_2$, 1 mM dihiothreitol (DTT), 0.1 mM ethylenediaminetetraacetic acid (EDTA), and 0.1 mM phenylmethylsulfonyl-fluoride (PMSF). The homogenate was mixed with 80 µl of 10% Nonidet P-40 (NP-40) solution and then centrifuged at 14,000×g for 2 min. The precipitates were washed once with 500 µl of Buffer-A plus 40 µl of 10% NP-40, centrifuged and re-suspended in 200 µl of buffer-C (50 mM HEPES, pH 7.8, 50 mM KCl, 300 mM NaCl, 0.1 mM EDTA, 1 mM DTT, 0.1 mM PMSF, and 20% glycerol), and re-centrifuged at 14,800×g for 5 min. The supernatant was collected and used for the determination of nuclear factor kappa B (NF-κB), tumor necrosis factor alpha (TNF-α), beta-carotene oxygenase 2 (BCO2), insulin receptor (IRS-1), peroxisome proliferator-activated receptor gamma (PPAR-γ), nuclear factor (erythroid-derived 2) related factor (Nrf-2) and heme oxygenase 1 (HO-1), according to known methods (e.g., Sahin et al., 2013). Briefly, equal amounts of protein (50 µg) were electrophoresed and subsequently transferred onto a nitrocellulose membrane (Schleicher and Schuell Inc., Keene, N.H., USA).

Antibodies against NF-κB, TNF-α, BCO2, IRS-1, PPAR-γ, Nrf-2 and HO-1 (Abcam, Cambridge, UK, were diluted (1:1000) in the same buffer containing 0.05% Tween-20. Protein loading was controlled using monoclonal mouse antibody against β-actin. Bands were analyzed densitometrically using Image J, an image analysis system (National Institute of Health, Bethesda, USA).

Statistical Analysis and Results

The data were analyzed using the GLM procedure of SAS (SAS Institute: SAS User's Guide: Statistics). The treatments were compared using ANOVA and student's unpaired t test, and $P<0.05$ was considered statistically significant.

Effect of MZ on Biochemical Indicators of Lipid Metabolism

TABLE 2

Effect of MZ supplementation on biochemical indicators in rats fed with HFD

| Item | Groups | | | | SEM |
|---|---|---|---|---|---|
| | Control | MZ | HFD | HFD + MZ | |
| Glucose (mg/dl) | 79.00 | 80.14 | 195.14 | 165.57 | 3.94 |
| Insulin (ng/mL) | 1.78 | 1.66 | 7.76 | 4.82 | 0.12 |
| FFA (mM) | 1.23 | 1.02 | 3.81 | 2.03 | 0.11 |
| Leptin (ng/mL) | 30.71 | 293.57 | 107.71 | 75.43 | 3.46 |
| Adiponectin (microgram/mL) | 10.37 | 11.02 | 5.97 | 8.63 | 0.24 |
| T-C (mg/ml) | 50.80 | 48.97 | 83.14 | 54.29 | 1.47 |
| HDL-C (mg/dl) | 17.14 | 14.71 | 20.43 | 19.43 | 0.66 |
| LDL-C (mg/dl) | 26.71 | 24.29 | 46.43 | 33.29 | 1.89 |
| TG (mg/dl) | 27.29 | 23.86 | 50.43 | 36.00 | 1.99 |

There was a significant increase in glucose, insulin, free fatty acid (FFA) and leptin in HFD fed rats. MZ supplementation caused a considerable decrease in increased levels of substances. The study reports an almost 50% decrease in adiponectin, and an increase in total cholesterol (T-C), high-density lipoprotein (HDL-C) and low-density lipoprotein (LDL-C), as well as triglycerides (TG) in HFD rats. The changes in these biochemical indicators of lipid metabolism were brought down to normal by MZ supplementation.

TABLE 3

Effect of MZ on serum and hepatic lipid peroxidation

| Item | Groups | | | | SEM |
|---|---|---|---|---|---|
| | Control | MZ | HFD | HFD + MZ | |
| Serum MDA (nmol/mL) | 0.87 | 0.73 | 1.88 | 1.56 | 0.05 |
| Liver MDA (nmol/mg protein) | 1.82 | 1.63 | 3.82 | 2.84 | 0.08 |
| Serum TAC (U/mL) | 1.18 | 1.28 | 0.46 | 0.74 | 0.07 |
| Liver SOD (U/mg protein) | 182.86 | 196.57 | 106.29 | 134.43 | 3.51 |
| Liver CAT (U/mg protein) | 299.71 | 313.57 | 253.43 | 276.43 | 9.33 |
| Liver GSHPx (U/mg protein) | 41.29 | 53.14 | 16.86 | 26.71 | 2.01 |

MZ supplementation caused a significant decrease in both serum (Serum MDA) and hepatic lipid peroxidation (Liver MDA), as measured by MDA nmol/ml.

The serum total antioxidant capacity (TAC), liver superoxide dismutase (SOD) and liver GPx (Liver GSHPx) decreased in HFD fed rats, but found to increase in MZ supplemented rats, although the increase does not return to the level seen in untreated or MZ alone treated control rats. The activity level of catalase (Liver CAT) also decreased in HFD rats and showed an increase in HFD rats supplemented with MZ. Increase in levels of all these liver antioxidant enzymes is useful for reduction of oxidative stress on liver.

TABLE 4

Effect of MZ on general nutrition parameters in HFD rats

| Item | Groups | | | | SEM |
|---|---|---|---|---|---|
| | Control | MZ | HFD | HFD + MZ | |
| Initial BW (g) | 233.86 | 234.43 | 232.29 | 234.43 | 4.68 |
| Final BW (g) | 286.29 (122%) | 291.71 (124.4%) | 340.86 (146.7%) | 326.29 (139%) | 6.34 |

TABLE 4-continued

Effect of MZ on general nutrition parameters in HFD rats

| Item | Groups | | | | SEM |
| --- | --- | --- | --- | --- | --- |
| | Control | MZ | HFD | HFD + MZ | |
| FI (g/d) | 23.54 | 23.31 | 19.16 | 19.28 | 0.53 |
| Visceral fat (g) | 7.79 | 7.69 | 29.54 | 15.33 | 0.75 |
| Liver (g) | 12.29 (4.29%) | 11.84 (4.05%) | 20.56 (6.03%) | 17.19 (5.26%) | 0.46 |

HFD caused a significant increase in visceral fat and liver weight; both of which reduced in MZ supplemented rats. The percent increase in body weight (BW) of 146.7% in HFD rats was reduced to 139% in MZ supplemented group. There was also a substantial increase registered in the liver weight: body weight ratio of HFD fed rats. MZ supplementation caused a decrease in this increased ratio.

Figure 2A:
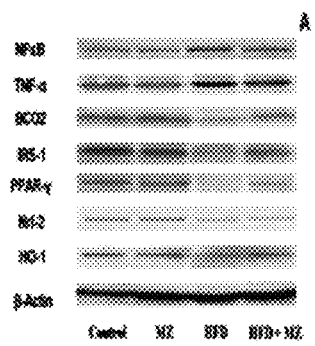
FIG. 2A shows Western blot strips of proteins measured.
Figure 2B:
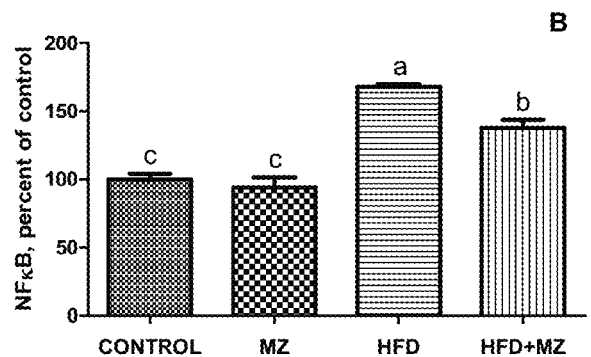
FIG. 2B to 2H show expression level of NF-κB, TNF-α, BCO2, IRS-1, PPAR-γ, Nrf-2 and HO-1 in various groups.
Figure 2C:
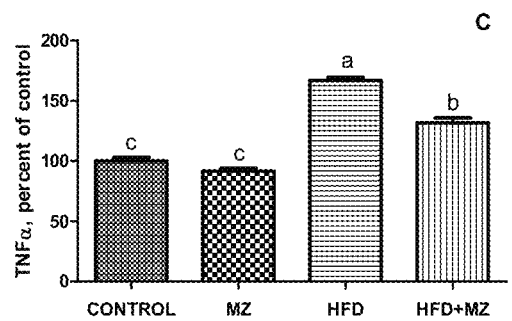
Figure 2D:
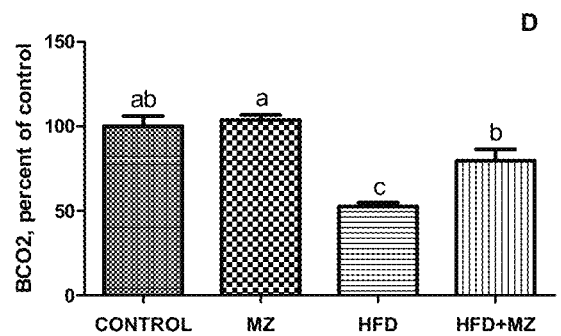
Figure 2E:
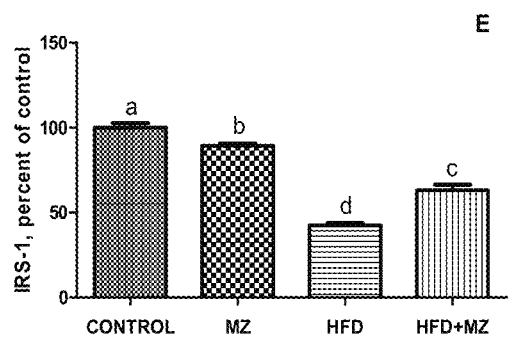
Figure 2F:
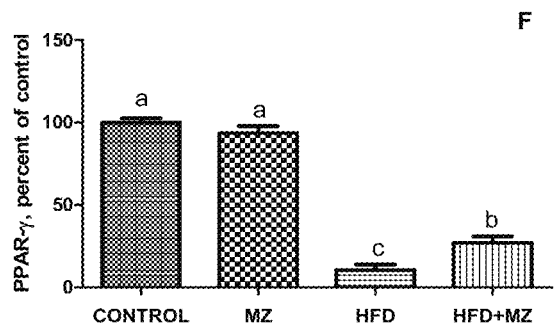
Figure 2G:
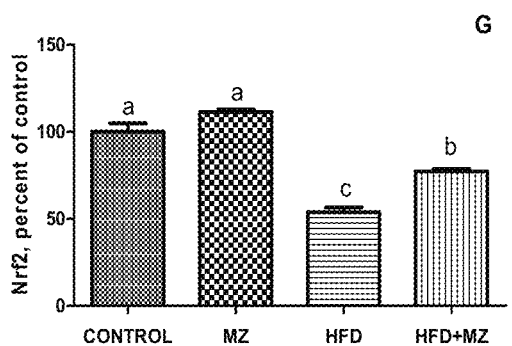
Figure 2H:
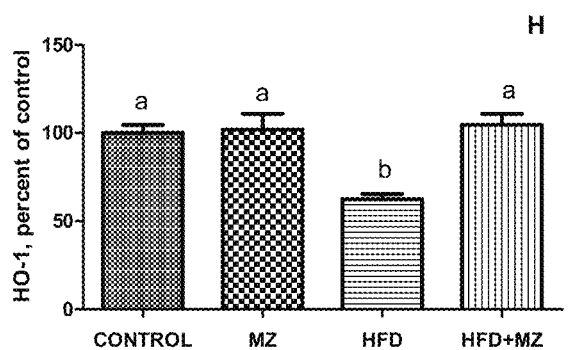

FIG. 2: Effect of MZ on the Expression of Hepatic Proteins NF-κB, TNF-α, BCO2, IRS-1, PPAR-γ, Nrf-2 and HO-1 in HFD fed rats MZ reduced the increased level of NF-κB, TNF-α in HFD fed rats. In MZ alone treated animals, the expression levels of these proteins were same as that of control group. On the other hand, MZ induced a significant increase in BCO2, IRS-1, PPAR-γ, Nrf-2 and HO-1 in HFD rats, when compared with the untreated HFD group. MZ supplementation caused a near normalization of the expression of HO-1 in HFD fed rats.

FIG. 2: Hepatic NF-κB, TNF-α, BCO2, IRS-1, PPAR-γ, Nrf-2 and HO-1 expression levels in meso-zeaxanthin (MZ) supplemented high fat diet (HFD) fed rats and control groups. The Western blot strips of the proteins measured in this study are shown in Panel A (FIG. 2A. Panels B-H (FIGS. 2B-2H) show the expression level of NF-κB, TNF-α, BCO2, IRS-1, PPAR-γ, Nrf-2 and HO-1 in various groups. The intensity of the bands shown in Panel B was quantified by densitometric analysis. Data are expressed as a ratio of normal control value (set to 100%). Each bar represents the mean and standard error of mean. Blots were repeated at least 3 times (n=3) and only a representative blot is shown in Panel A. β-Actin was included to ensure equal protein loading.

Meso-zeaxanthin significantly alleviated cardio-metabolic health markers and decreased inflammatory markers. The treatment increased the level of antioxidant enzymes (catalase, superoxide dismutase and glutathione peroxidase) and also helped to improve the liver function, possibly through enhancement of the detoxification process. Taken together, the results of the study suggested MZ as a potential substance that can be considered as an adjunct therapy in fatty liver and prevention of cardiometabolic syndrome.

We claim:

1. A method for treating non-alcoholic fatty liver disease in a subject fed a high fat diet, comprising administering to said subject an effective amount of a meso-zeaxanthin composition comprising at least 80% by weight of (trans, 3R, 3'S, meso)-zeaxanthin based on a total xanthophyll content of the composition.

2. The method of claim 1, wherein the effective amount of the meso-zeaxanthin composition administered to the subject is about 0.1 to about 200 mg/kg body weight.

3. The method of claim 1, further comprising comparing the relative liver health of said subject administered said meso-zeaxanthin composition and fed a high fat diet to the relative liver health of a subject administered a high fat diet alone by measuring and comparing one or more biochemical parameters of said subjects selected from the group consisting of lipid content in the liver levels of cholesterol and triglycerides liver weight visceral fat liver:body weight ration, antioxidant enzyme levels, and levels of malondialdehyde (MDA).

* * * * *